(12) United States Patent
Hopkinson et al.

(10) Patent No.: US 10,130,797 B2
(45) Date of Patent: Nov. 20, 2018

(54) BALLOON CATHETER SYSTEMS AND METHODS

(71) Applicant: Merit Medical Systems, Inc., South Jordan, UT (US)

(72) Inventors: Aaron J. Hopkinson, Herriman, UT (US); Hugh W. Goldston, West Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 509 days.

(21) Appl. No.: 14/341,261

(22) Filed: Jul. 25, 2014

(65) Prior Publication Data

US 2015/0032086 A1    Jan. 29, 2015

Related U.S. Application Data

(60) Provisional application No. 61/858,451, filed on Jul. 25, 2013.

(51) Int. Cl.
*A61M 25/10* (2013.01)
*A61M 25/00* (2006.01)
(Continued)

(52) U.S. Cl.
CPC .......... *A61M 25/10* (2013.01); *A61M 25/005* (2013.01); *A61M 25/0032* (2013.01); *A61M 25/0097* (2013.01); *A61M 25/002* (2013.01); *A61M 25/0052* (2013.01); *A61M 25/09041* (2013.01); *A61M 25/1006* (2013.01); *A61M 2025/0059* (2013.01); *A61M 2025/0063* (2013.01); *A61M 2025/0177* (2013.01);
(Continued)

(58) Field of Classification Search
CPC ...... A61M 25/1006; A61M 2025/0177; A61M 2025/1056; A61M 2025/1061; A61M 25/005; A61M 25/0052; A61M 25/0097; A61M 25/09041; A61M 25/10; A61M 2025/0059; A61M 2025/0063
USPC ............. 604/103.09, 509; 606/191, 194, 198
See application file for complete search history.

(56) References Cited

U.S. PATENT DOCUMENTS

| | | | |
|---|---|---|---|
| 4,976,690 A | | 12/1990 | Solar et al. |
| 5,087,246 A | * | 2/1992 | Smith ............... A61M 25/1002 604/103 |

(Continued)

FOREIGN PATENT DOCUMENTS

| | | |
|---|---|---|
| EP | 0344530 | 5/1989 |
| EP | 0528294 | 8/1992 |

(Continued)

OTHER PUBLICATIONS

U.S. Appl. No. 14/341,203, filed Jul. 25, 2014, Hopkinson et al.
(Continued)

*Primary Examiner* — Katherine M Shi
(74) *Attorney, Agent, or Firm* — Stoel Rives LLP

(57) ABSTRACT

The embodiments disclosed herein relate to balloon catheter assemblies. The balloon catheter assemblies can include a hub, an elongated member, and an inflation balloon. The balloon catheter assemblies can also include a support wire having a proximal end that is longitudinally displaceable within a sleeve that is disposed in the catheter hub. A distal end of the support wire may be coupled to the inflation balloon at one or more positions.

11 Claims, 9 Drawing Sheets

(51) Int. Cl.
*A61M 25/09* (2006.01)
*A61M 25/01* (2006.01)
(52) U.S. Cl.
CPC ............... *A61M 2025/1056* (2013.01); *A61M 2025/1061* (2013.01)

(56) References Cited

U.S. PATENT DOCUMENTS

| | | | |
|---|---|---|---|
| 5,171,222 A * | 12/1992 | Euteneuer | A61M 25/104 |
| | | | 604/103.1 |
| 5,318,529 A | 6/1994 | Kontos | |
| 5,423,754 A | 6/1995 | Cornelius et al. | |
| 5,480,383 A | 1/1996 | Bagaoisan et al. | |
| 5,569,184 A | 10/1996 | Crocker et al. | |
| 5,728,063 A | 3/1998 | Preissman et al. | |
| 5,746,745 A | 5/1998 | Abele et al. | |
| 5,820,613 A | 10/1998 | Van Werven-Franssen et al. | |
| 5,906,606 A | 5/1999 | Chee et al. | |
| 6,146,354 A | 11/2000 | Beil | |
| 6,280,545 B1 * | 8/2001 | Kanesaka | A61M 25/1029 |
| | | | 156/381 |
| 6,322,534 B1 | 11/2001 | Shkolnik | |
| 8,690,824 B2 | 4/2014 | Holman et al. | |
| 2002/0068922 A1 | 6/2002 | Peters | |
| 2003/0014008 A1 | 1/2003 | Jacques | |
| 2003/0236495 A1 | 12/2003 | Kennedy, II | |
| 2004/0039369 A1 | 2/2004 | Shelso | |
| 2004/0092867 A1 | 5/2004 | Murray, III | |
| 2004/0092868 A1 | 5/2004 | Murray | |
| 2004/0236366 A1 * | 11/2004 | Kennedy, II | A61M 25/10 |
| | | | 606/192 |
| 2005/0107821 A1 | 5/2005 | Shanley et al. | |
| 2005/0137617 A1 | 6/2005 | Kelley et al. | |
| 2005/0288628 A1 | 12/2005 | Jordan et al. | |
| 2007/0129748 A1 | 6/2007 | Eidenschink et al. | |
| 2007/0270935 A1 | 11/2007 | Newhauser et al. | |
| 2007/0288053 A1 | 12/2007 | Trotta | |
| 2010/0030141 A1 | 2/2010 | Chermoni | |
| 2010/0185145 A1 | 7/2010 | Pepper et al. | |
| 2011/0288478 A1 | 11/2011 | Ehrenreich et al. | |
| 2012/0209176 A1 | 8/2012 | Anderson | |
| 2013/0197563 A1 * | 8/2013 | Saab | A61M 29/02 |
| | | | 606/191 |

FOREIGN PATENT DOCUMENTS

| | | |
|---|---|---|
| EP | 0611582 | 1/1994 |
| EP | 2170452 | 1/2009 |
| WO | PCT/US2014/048204 | 7/2014 |
| WO | PCT/US20140/48193 | 7/2014 |

OTHER PUBLICATIONS

International Search Report and Written Opinion dated Nov. 5, 2014 for PCT/US2014/048193.
International Search Report and Written Opinion dated Nov. 11, 2014 for PCT/US2014/048204.
Office Action dated Sep. 16, 2016 for U.S. Appl. No. 14/341,203.
Office Action dated Mar. 9, 2017 for U.S. Appl. No. 14/341,203.
European Search Report dated Jun. 21, 2017 for EP14829001.8.
European Search Report dated Mar. 20, 2017 for EP14829001.8.
Office Action dated Sep. 12, 2017 for U.S. Appl. No. 14/341,203.

* cited by examiner

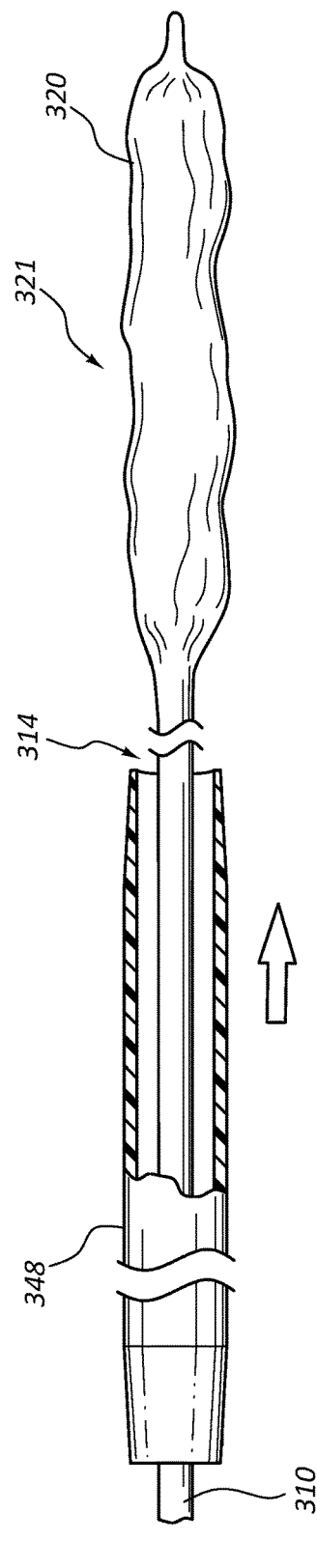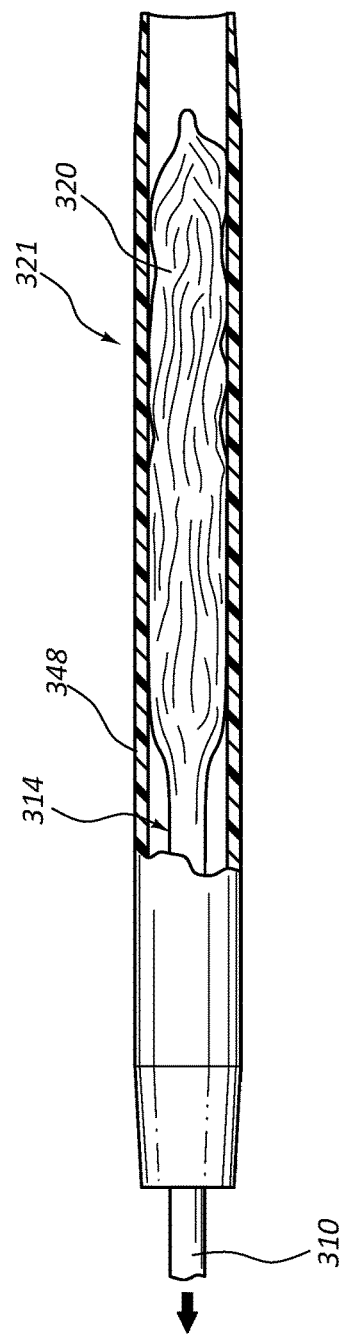
FIG. 8
FIG. 9

BALLOON CATHETER SYSTEMS AND METHODS

RELATED APPLICATION

This application claims priority to U.S. Provisional Application No. 61/858,451, filed on Jul. 25, 2013, titled BALLOON CATHETER SYSTEMS AND METHODS, which is hereby incorporated by reference in its entirety.

TECHNICAL FIELD

The present disclosure relates generally to catheters. More specifically, the present disclosure relates to balloon catheter assemblies and methods of use.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

FIG. 8 is a perspective view of the portion of the balloon catheter assembly of FIG. 6, depicted in an unpackaged and deflated configuration.

FIG. 9 is a perspective view of the portion of the balloon catheter assembly of FIG. 6, depicted in a repackaged configuration.

DETAILED DESCRIPTION

Figure 1:
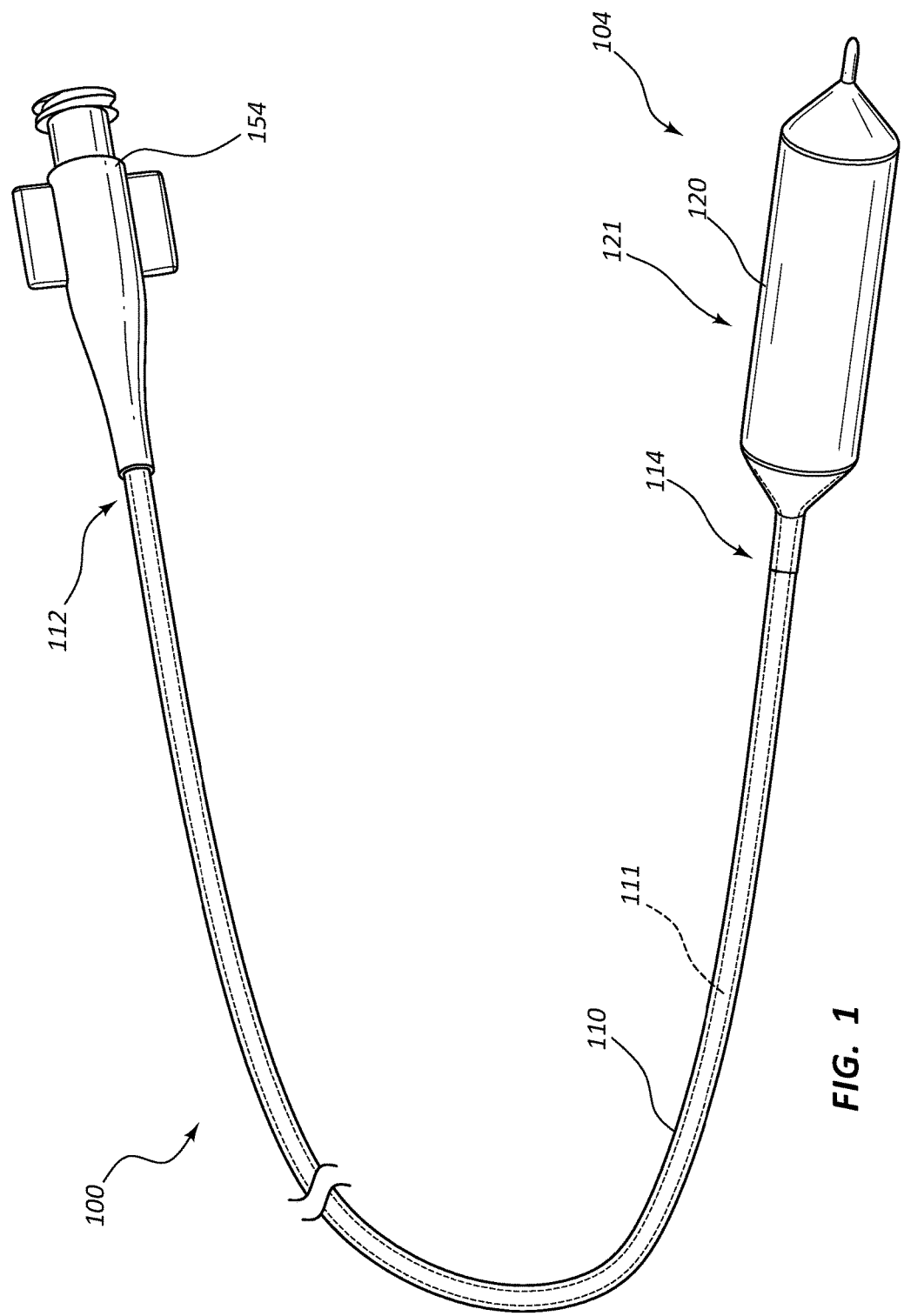
FIG. 1 is a perspective view of a balloon catheter assembly, according to one embodiment of the present disclosure.

The various embodiments disclosed herein generally relate to catheters. More specifically, the various embodiments relate to balloon catheter systems, for example, balloon catheter assemblies, fixed wire balloon catheter assemblies, and related methods. In some embodiments, the balloon catheter assembly comprises a hub, an elongated member, an inflation balloon, and a support wire. Also disclosed herein are methods of unpackaging, utilizing, and repackaging a balloon catheter assembly.

Balloon catheter assemblies may also comprise a sleeve, wherein the sleeve may be disposed within the hub of the balloon catheter assembly. A proximal end of the support wire may be displaceable within the sleeve. For example, during insertion of the balloon catheter assembly, the support wire may transition to a position wherein the proximal end of the support wire abuts a proximal end of the sleeve. During removal of the balloon catheter assembly, the support wire may transition to a position wherein the proximal end of the support wire is distally removed from the proximal end of the sleeve.

It will be appreciated that various features are sometimes grouped together in a single embodiment, figure, or description thereof for the purpose of streamlining the disclosure. Many of these features may be used alone and/or in combination with one another. It will further be appreciated that many of the features disclosed herein may be used in conjunction with other catheter assemblies presently known or hereafter developed.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal portion of a medical device is the portion nearest a practitioner during use, while the distal portion is a portion at the opposite end. For example, the proximal end of a balloon catheter assembly is defined as the end closest to the practitioner during insertion or utilization of the balloon catheter assembly. The distal end is the end opposite the proximal end, along the longitudinal direction of the balloon catheter assembly.

FIG. 1 illustrates a balloon catheter assembly 100 according to one embodiment of the present disclosure. The balloon catheter assembly 100 comprises a hub 154, an elongated member 110, and an inflation balloon 120. The elongated member 110 may be configured to provide a passageway for components and/or substances between at least the hub 154 and the inflation balloon 120. For example, in the illustrated embodiment, a distal end 114 of the elongated member 110 is coupled to the balloon segment 121, which comprises the inflation balloon 120, and a proximal end 112 of the elongated member 110 is coupled to the hub 154.

In the illustrated embodiment, the elongated member 110 comprises a lumen 111 extending longitudinally therethrough. For example, the lumen 111 can be configured to serve as a passageway through which an inflation fluid (e.g., a gas or a liquid) may be introduced into and/or withdrawn from the inflation balloon 120. In such embodiments, the lumen 111 may be referred to as an inflation/deflation lumen.

In some other embodiments, the elongated member 110 may comprise a plurality of lumens extending longitudinally therethrough.

In certain embodiments, the elongated member 110 comprises a polymeric material. The polymeric material may be extruded to form the elongated member 110 using one or more extrusion techniques. The elongated member 110 may also be referred to as catheter tubing, an elongated tubular member, a tubular member, or a first tubular member.

The inflation balloon 120 is disposed at a distal portion 104 of the balloon catheter assembly 100. An interior of the inflation balloon 120 is in fluid communication with the lumen 111 of the elongated member 110 (i.e., the inflation/deflation lumen). For example, inflation fluid may flow between the inflation/deflation lumen 111 of the elongated member 110 and the inflation balloon 120, or the interior thereof, during both inflation and deflation procedures, as discussed further below.

Figure 2:
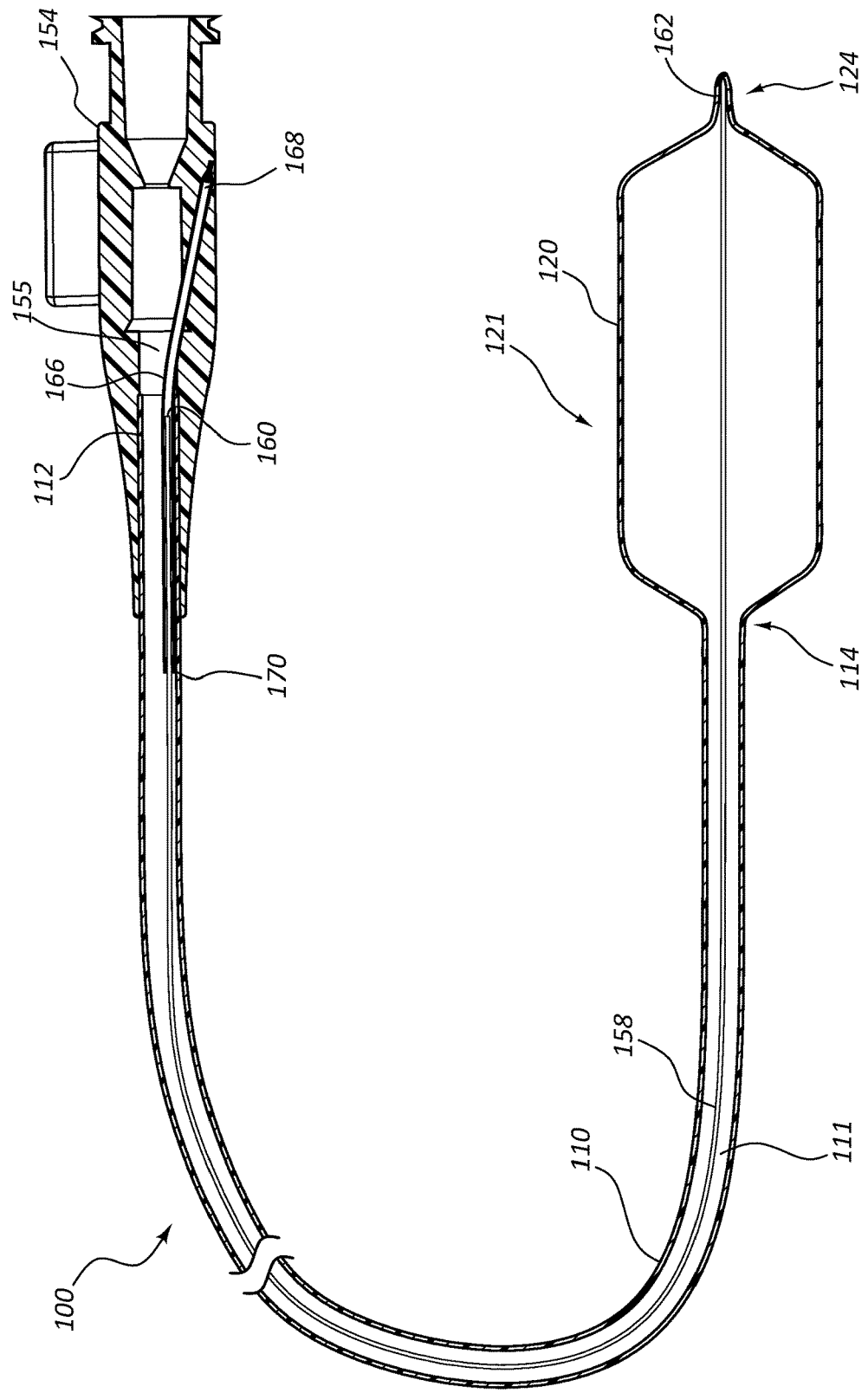
FIG. 2 is a cross-sectional view of the balloon catheter assembly of FIG. 1.

FIG. 2 is a cross-sectional view of the balloon catheter assembly 100 of FIG. 1. As discussed above, the balloon catheter assembly 100 comprises the inflation balloon 120, the elongated member 110, and the hub 154. As further shown, the proximal end 112 of the elongated member 110 is coupled to the hub 154, and the distal end 114 of the elongated member 110 is coupled to the balloon segment 121. The balloon catheter assembly 100 further comprises a support wire 158 and a sleeve 166.

In some embodiments, the support wire 158 is at least partially disposed within the lumen 111 of the elongated member 110. For example, in the illustrated embodiment, the support wire 158 extends longitudinally within the lumen 111 of the elongated member 110 and into the inflation balloon 120, or the interior of the inflation balloon 120. In such embodiments, the support wire 158 is configured to add increased rigidity and/or stiffness to the elongated member 110 and/or the inflation balloon 120, which may aid in insertion of the balloon catheter assembly 100 into a delivery lumen (e.g., an endoscope) and/or a body lumen during use by a practitioner. As further illustrated, a distal end 162 of the support wire 158 may be coupled to, fixedly coupled to, or attached to the distal end 124 of the inflation balloon 120. Also, as depicted, a proximal end 160 of the support wire 158 is at least partially disposed within the sleeve 166. In some embodiments, the proximal end 160 of the support wire 158 may be operatively coupled to the hub 154 and/or the sleeve 166 such that the support wire 158 transfers distally oriented forces exerted on the hub 154 but not proximally oriented forces exerted on the hub 154 (i.e., distally and/or proximally oriented forces exerted by a practitioner on the hub 154 during use of the balloon catheter assembly 100, such as during a medical procedure, as described in more detail below). In some other embodiments, the proximal end 160 of the support wire 158 can be fixedly coupled to the hub 154. In various embodiments, the illustrated balloon catheter assembly 100 may be referred to as a fixed wire balloon catheter assembly, as the support wire 158 may not be configured, nor intended, to be removed from the balloon catheter assembly 100.

The support wire 158 may be operatively coupled to the balloon catheter assembly 100 such that the support wire 158 does not exert a longitudinally compressive force on the inflation balloon 120 and such that the support wire 158 longitudinally supports the inflation balloon 120 when the inflation balloon 120 is subjected to longitudinally compressive forces. For example, the support wire 158 of the balloon catheter assembly 100 may be configured such that the inflation balloon 120 resists longitudinal compression upon insertion or passage of the inflation balloon 120 into or through a delivery lumen and/or a body lumen.

In the illustrated embodiment of FIG. 2, the sleeve 166 is at least partially disposed within the hub 154 of the balloon catheter assembly 100. In some embodiments, the sleeve 166 is coupled to, fixedly coupled to, retained within, or attached to an inside of the hub 154. For example, the sleeve 166 may be partially disposed or embedded into an inner wall of the hub 154. In other embodiments, the sleeve 166 is partially molded within an inner wall of the hub 154. In yet other embodiments, a portion of the sleeve 166 is forcibly inserted into an inner wall of the hub 154.

The sleeve 166 may comprise a hollow tubular structure. The distal end 170 of the sleeve 166 is open. In some embodiments, the proximal end 168 of the sleeve 166 is closed. For example, the proximal end 168 of the sleeve 166 may be crimped closed. In other embodiments, the proximal end 168 of the sleeve 166 may be open.

The sleeve 166 may comprise a rigid material, such as a metal material. In other embodiments, a hard polymeric material may be used. Other materials may also be used. In some embodiments, the sleeve 166 is about an inch long; however, other lengths may also be used. For example, the sleeve 166 may be larger or smaller depending on the size and type of the catheter for which it is configured.

In some other embodiments, the balloon catheter assembly 100 may not comprise a sleeve 166. For example, the proximal end 160 of the support wire 158 may be operatively coupled to the hub 154 at the lumen 155 of the hub 154 or at another position in or adjacent to the hub 154.

Figure 3A:
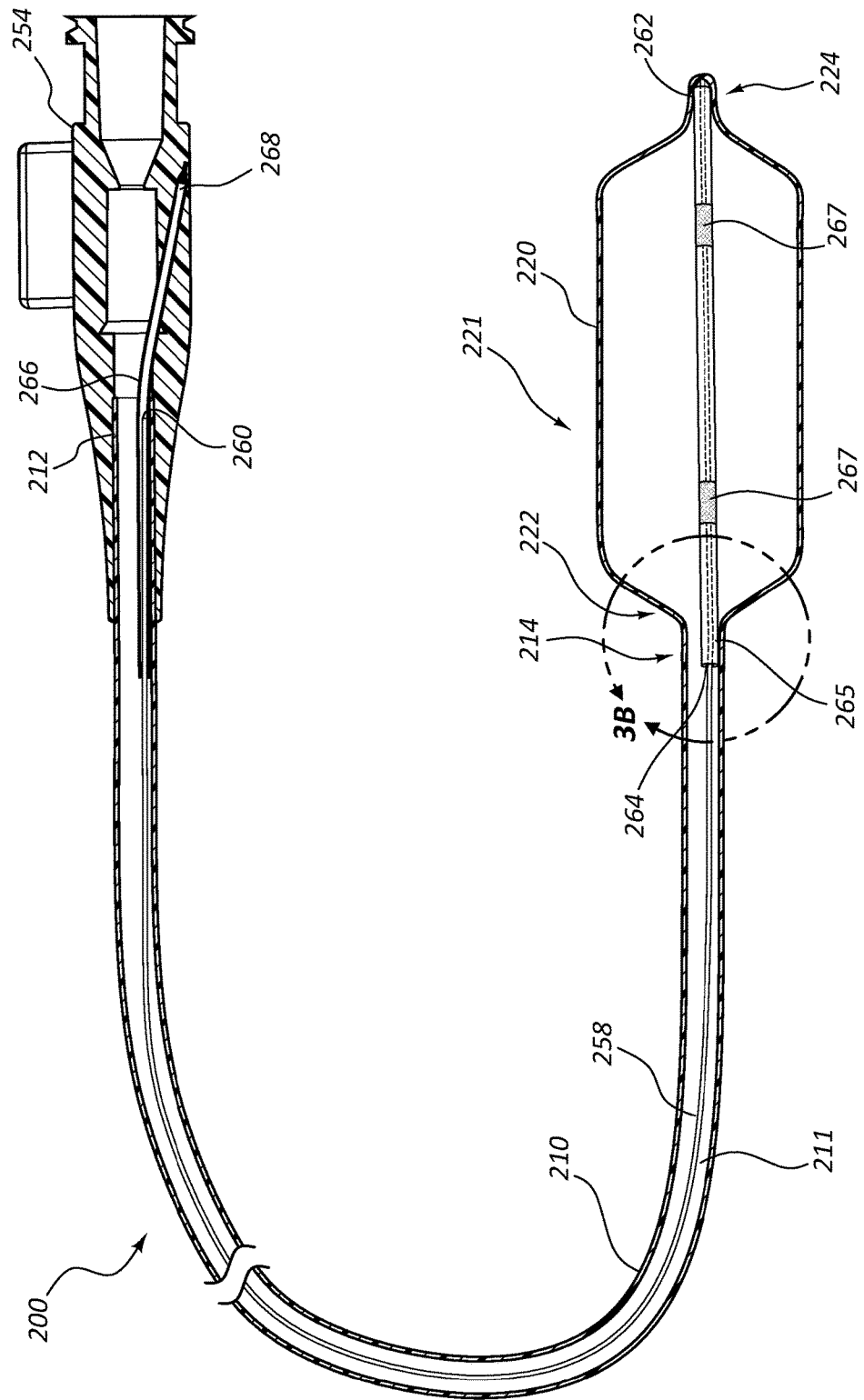
FIG. 3A is a cross-sectional view of a balloon catheter assembly, according to another embodiment of the present disclosure.

FIG. 3A illustrates a cross-sectional view of another embodiment of a balloon catheter assembly that can, in certain respects, resemble components of the balloon catheter assembly described in connection with FIGS. 1 and 2. It will be appreciated that all the illustrated embodiments may have analogous features. Accordingly, like features are designated with like reference numerals, with the leading digits incremented to "2." For instance, the inflation balloon is designated "120" in FIGS. 1 and 2, and an analogous inflation balloon is designated as "220" in FIG. 3A. Relevant disclosure set forth above regarding similarly identified features thus may not be repeated hereafter. Moreover, specific features of the balloon catheter assembly and related components shown in FIGS. 1 and 2 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the balloon catheter assembly of FIG. 3A. Any suitable combination of the features, and variations of the same, described with respect to the balloon catheter assembly and components illustrated in FIGS. 1 and 2 can be employed with the balloon catheter assembly and components of FIG. 3A, and vice versa. This pattern of disclosure applies equally to further embodiments depicted in subsequent figures and described hereafter.

The balloon catheter assembly 200 of FIG. 3A comprises an elongated member 210. As illustrated, and as discussed above in reference to FIGS. 1 and 2, the elongated member 210 comprises a lumen 211 extending longitudinally through the elongated member 210. A balloon segment 221 is coupled to a distal end 214 of the elongated member 210. In various embodiments, the elongated member 210 and the inflation balloon 220 may be integrally formed. In other embodiments, the elongated member 210 and the inflatable balloon 220 may be separately formed. Further, a hub 254 is coupled to a proximal end 212 of the elongated member 210. The balloon catheter assembly 200, as depicted, also comprises a support wire 258 disposed within at least a portion of the elongated member 210. In some embodiments, a distal end 262 of the support wire 258 is coupled to a distal end 224 of the inflation balloon 220. A proximal end 260 of the support wire 258 may be disposed within at least a portion of the hub 254, wherein the proximal end 260 of the support wire 258 may be longitudinally displaceable within the hub 254. In some embodiments, at least a portion of the proximal end 260 of the support wire 258 may be disposed within at least a portion of the hub 254 such that the support wire 258 does not transfer, or is not configured to transfer, a proximal longitudinal force to the inflation balloon 220.

The distal end 262 of the support wire 258, as depicted in FIG. 3A, is coupled to a distal end 224 of the inflation balloon 220. Additionally, a coupling portion 264 of the support wire 258 is coupled to a proximal end 222 of the inflation balloon 220 and/or a distal end 214 of the elongated member 210. In certain embodiments, the support wire 258 may also, or alternatively, be coupled to the inflation balloon 220 and/or the elongated member 210 at other positions. In such embodiments, the support wire 258 may resist, or be configured to resist, longitudinal compression of the inflation balloon 220. Stated another way, the support wire 258 may be coupled to the inflation balloon 220 such that a longitudinal compression of the inflation balloon 220 is at least partially inhibited when the inflation balloon 220 is being inserted into or withdrawn from a delivery lumen and/or a body lumen. Coupling of the support wire 258 to at least each of the proximal end 222 and the distal end 224 of the inflation balloon 220 may longitudinally support the inflation balloon 220, as the inflation balloon 220 in such a configuration cannot substantially be longitudinally compressed without deforming at least a portion or a segment of the support wire 258 disposed between each of the proximal end 222 and the distal end 224 of the inflation balloon 220.

Figure 3B:
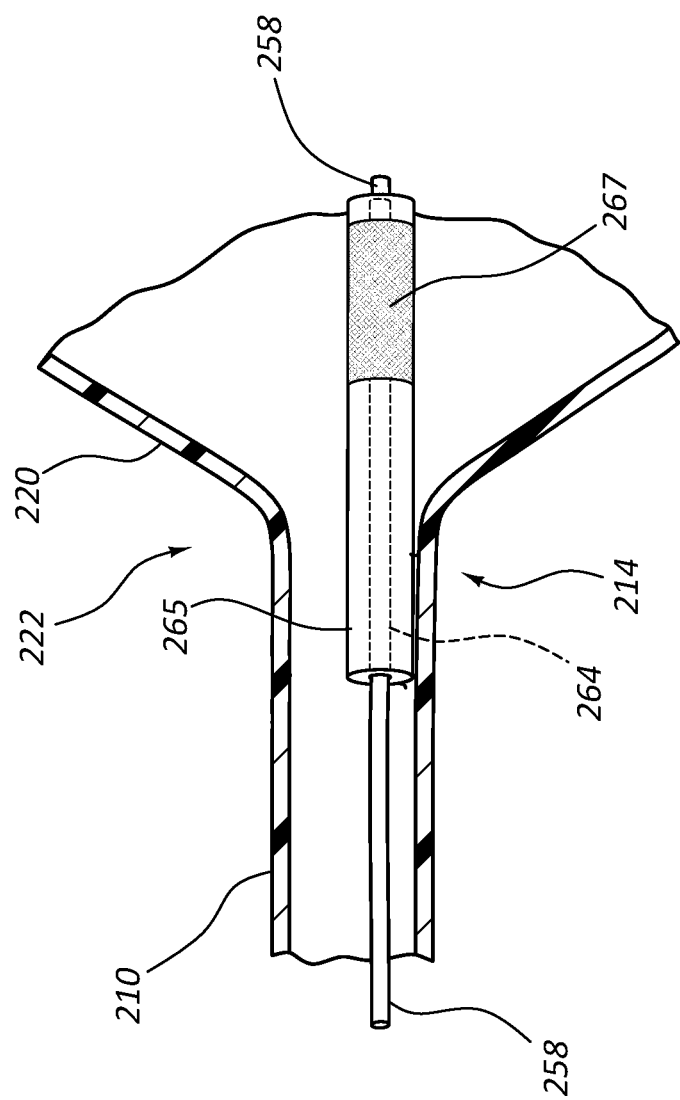
FIG. 3B is a detail view, taken through the line 3B, of a portion of the balloon catheter assembly of FIG. 3A.

FIG. 3B is a detail view, taken through line 3B, of a portion of the balloon catheter assembly 200 of FIG. 3A. Referring to FIGS. 3A and 3B, the coupling portion 264 of the support wire 258 can be disposed, or at least partially disposed, within a second tubular member 265. In certain embodiments, the coupling portion 264 of the support wire 258 may be coupled, or fixedly coupled, to the second tubular member 265. As depicted, the coupling portion 264 of the support wire 258 is coupled to the distal end 214 of the elongated member 210 via the second tubular member 265.

Additionally, in the illustrated embodiment, the second tubular member 265 extends to the distal end 224 of the inflation balloon 220. The second tubular member 265 may be bonded to the proximal end 222 and the distal end 224 of the inflation balloon 220, thus securing the support wire 258 to the proximal end 222 and the distal end 224 of the inflation balloon 220. In other embodiments, the second tubular member 265 may be shorter and/or may be coupled to just the proximal end 222 of the inflation balloon 220 or the distal end 224 of the inflation balloon 220. Any embodiment wherein the second tubular member 265 or support wire 258 is coupled to the proximal end 222 of the inflation balloon 220 may be altered such that these elements are coupled to the distal end 214 of the elongated member 210. Further, embodiments wherein the second tubular member 256 is shorter, and only coupled to the proximal end 222 of the inflation balloon 220, may further comprise another second tubular member, similar to the second tubular member 265, which may be positioned at the distal end 262 of the support wire 258 and may aid in coupling of the distal end 262 of the support wire 258 to the distal end 224 of the inflation balloon 220. Second tubular members may also be utilized at other positions wherein the support wire 258 is coupled to a component of the balloon catheter assembly 200. Such embodiments may enhance or improve the coupling of the support wire 258 to the inflation balloon 220 compared to some other embodiments lacking a second tubular member 265. For example, when the coupling portion 264 of the support wire 258 is directly coupled to the elongated member 210 and/or the inflation balloon 220, only a portion of a circumferential surface area of the coupling portion 264 may be coupled to or in contact with the elongated member 210 and/or the inflation balloon 220. In contrast, when the coupling portion 264 of the support wire 258 is disposed within the second tubular member 265, a greater portion of the circumferential surface area, or substantially all of the circumferential surface area, of the coupling portion 264 can be coupled to or in contact with the second tubular member 265. Further, the second tubular member 265, due at least in part to its greater diameter relative to a diameter of the coupling portion 264, may then have a larger circumferential surface area relative to the circumferential surface area of the coupling portion 264, that may be coupled to or in contact with the elongated tubular member 210 and/or the inflation balloon 220.

In certain embodiments, the second tubular member 265 may be coupled (e.g., bonded or welded) to the distal end 214 of the elongated member 210 and/or the proximal end 222 of the inflation balloon 220. In various embodiments, the support wire 258 may comprise a first material, and the second tubular member 265 may comprise a second material. For example, the support wire 258 may comprise a metal material, and the second tubular member 265 may comprise a polymeric material, or vice versa. For example, the second tubular member 265 may comprise a polymeric material, such as PEBAX, nylon, etc. Other suitable materials are also contemplated.

In other embodiments, the support wire 258, or the coupling portion 264 of the support wire 258, may be directly coupled to the elongated member 210 and/or the inflation balloon 220. For example, no second tubular member 265 may be present in some embodiments.

At least a portion of the support wire 258 and/or at least a portion of the second tubular member 265 may comprise one or more radiopaque markers 267. For example, at least a portion of the second tubular member 265 may comprise a radiopaque marker band 267. A radiopaque marker, such as the radiopaque marker bands 267, may assist the practitioner in positioning the inflation balloon 220 at a target site (e.g., at the location of an obstructed vessel) within a body lumen during use of the balloon catheter assembly 200. Also, in certain embodiments, a radiopaque marker, such as the radiopaque marker band 267, may crimp or secure the second tubular member 265 to the support wire 258. Additionally or alternatively the second tubular member 265 may be crimpled around the support wire 258 independently of a radiopaque maker band 267.

Coupling of the support wire 258 at or adjacent to each of the proximal end 222 and the distal end 224 of the inflation balloon 220 can ease disposition or insertion of the inflation balloon 220 into or through a delivery lumen and/or a body lumen of a patient. The support wire 258, in such embodiments, can stabilize and/or increase the rigidity of the inflation balloon 220. During disposition of inflation balloons through delivery lumens and/or body lumens, the inflation balloons may tend to longitudinally fold or collapse (i.e., in the manner of an accordion) due to, for example, a longitudinally compressive force. The configuration of the support wire 258 and the inflation balloon 220 as disclosed herein may act to inhibit or limit such folding or collapsing of the inflation balloon 220 upon displacement of the inflation balloon 220 through a delivery lumen and/or a body lumen (i.e., to a position at or adjacent a target site).

As described in reference to FIGS. 1 and 2, the illustrated balloon catheter assembly 200 of FIG. 3A also comprises a sleeve 266 that is coupled to, fixedly coupled to, or attached to the inside of the hub 254 (i.e., at least partially disposed inside an inner wall of the hub 254). Further, the proximal end 260 of the support wire 258 is disposed within at least a portion of the sleeve 266, wherein the proximal end 260 of the support wire 258 is longitudinally displaceable within the sleeve 266. In some embodiments, the proximal end 260 of the support wire 258 can abut, or be configured to abut, a proximal end 268 of the sleeve 266 when the inflation balloon 220 is being inserted into a delivery lumen and/or a body lumen (i.e., by a practitioner).

Figure 4:
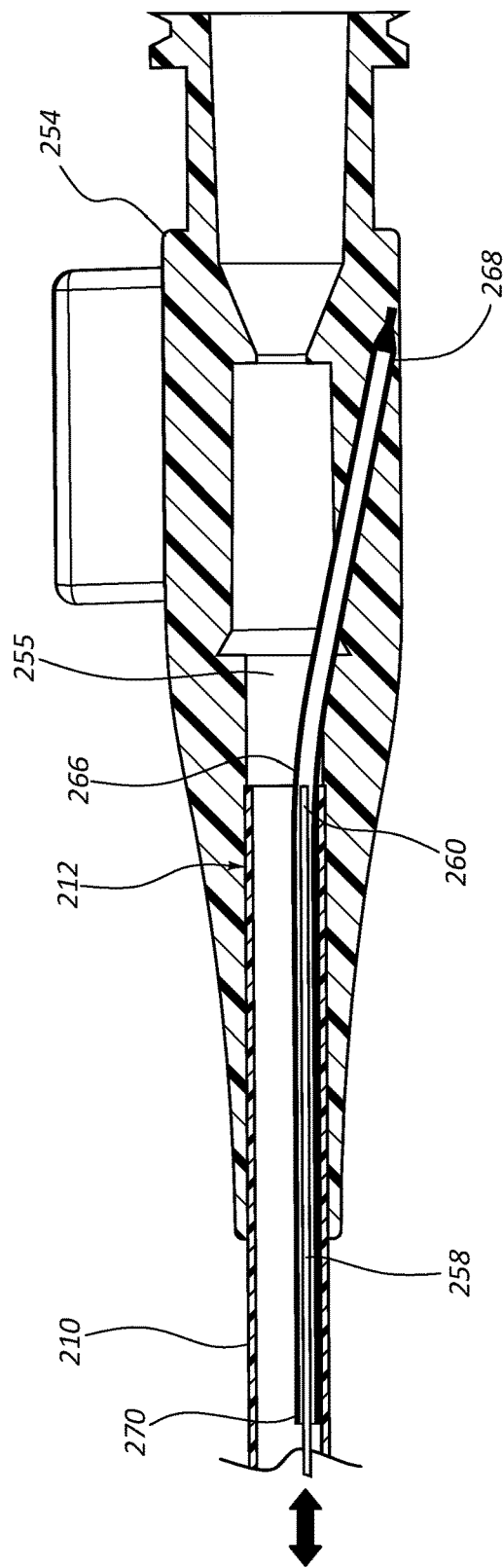
FIG. 4 is a cross-sectional view of a portion of the balloon catheter assembly of FIG. 3A in a first configuration.
Figure 5:
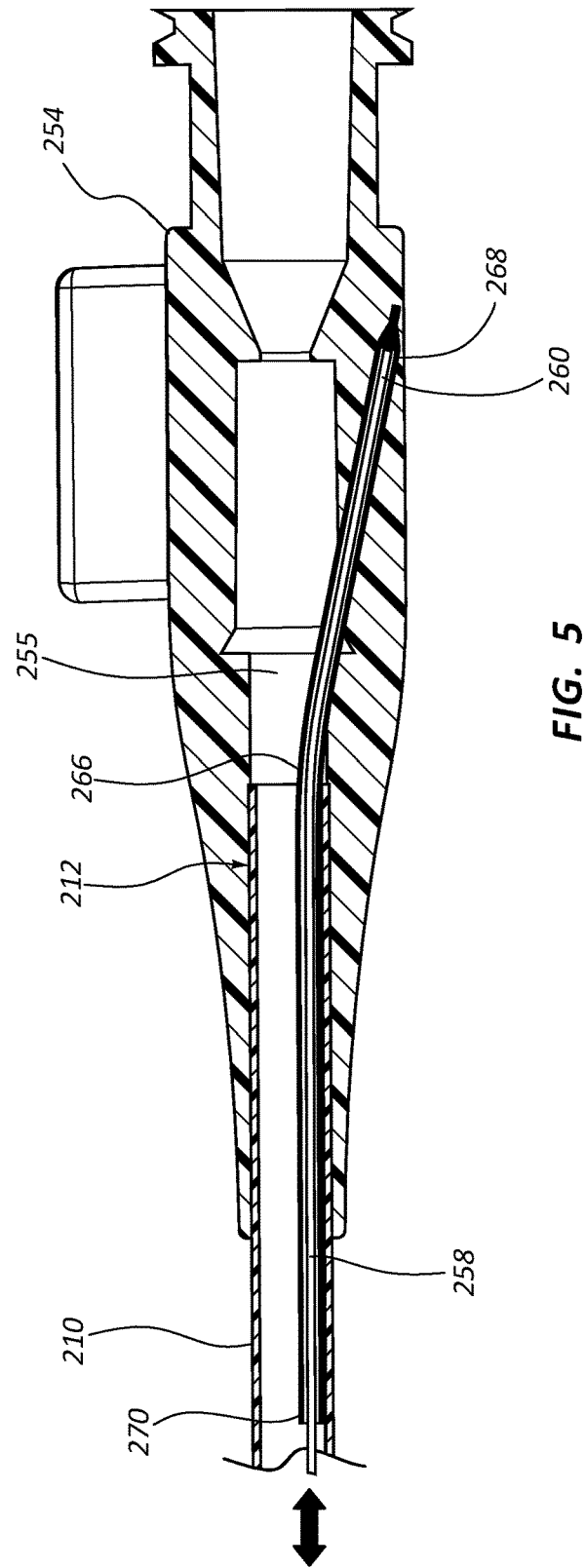
FIG. 5 is a cross-sectional view of a portion of the balloon catheter assembly of FIG. 3A in a second configuration.

FIGS. 4 and 5 illustrate the hub 254 of the balloon catheter assembly 200 of FIG. 3A in a first configuration and a second configuration, respectively. As shown, the sleeve 266 is at least partially disposed within the hub 254. For example, the proximal end 268 of the sleeve 266 comprises a sharp point that has been inserted into an inner wall of the hub 254. The proximal end 268 of the sleeve 266 is also closed. However, as previously stated, in other embodiments the proximal end 268 of the sleeve 266 could be open. In such embodiments, the open proximal end 268 of the sleeve 266 may abut material within the inner wall of the hub 254 to prevent proximal movement of the support wire 258 beyond the proximal end 268 of the sleeve 266.

As further illustrated, the proximal end 268 of the sleeve 266 is disposed at an angle that is offset from a lumen 255 of the hub 254. The sleeve 266 is also bent. In other embodiments, the sleeve 266 may be straight, or substantially straight. In such embodiments, the proximal end 268 of the straight, or substantially straight, sleeve 266 may be inserted into the inner wall of the hub 254, for example, at an angle that is offset from the lumen 255 of the hub 254.

As further illustrated in FIGS. 4 and 5, the distal end 270 of the sleeve 266 may extend distally into the proximal end 212 of the elongated member 210 and/or beyond the hub 254. The distal end 270 of the sleeve 266 is open and the support wire 258 extends from within the elongated member 210 to the inside of the sleeve 266. In the illustrated embodiment, the proximal end 260 of the support wire 258 is disposed within the sleeve 266. The support wire 258 is not fixedly coupled to the sleeve 266. Further, the support wire 258 is longitudinally displaceable within the sleeve 266, as indicated by the reference arrows. For example, as the elongated member 210 is inserted into a delivery lumen and/or a body lumen, resistance on the elongated member 210 may cause the support wire 258 to transition or otherwise move proximally toward the proximal end 268 of the sleeve 266. Once the support wire 258 abuts the proximal end 268 of the sleeve 266, it is no longer proximally displaceable (see FIG. 5). At this position, the support wire 258 may provide increased support and strength to the elongated member 210 during insertion into the delivery lumen and/or the body lumen.

After use, the inflation balloon may be deflated and the elongated member 210 may be withdrawn from the delivery lumen and/or the body lumen. In some instances, removal of the balloon catheter assembly requires force. For example, the deflated inflation balloon may have a tendency to catch or snag on introducer sheaths, scopes, and/or other insertion devices. The forces applied during removal may also cause the elongated member 210 to stretch. For example, the elongated member 210 may stretch longitudinally or otherwise become elongated in response to the removal forces that are being applied.

As the elongated member 210 elongates, the support wire 258, which is coupled to the proximal end and/or the distal end of the inflation balloon, may transition and/or move distally within the sleeve 266. For example, the support wire 258 moves distally from a position wherein the proximal end 260 of the support wire 258 is adjacent to, or closer to, the proximal end 268 of the sleeve 266, as illustrated in FIG. 5, to a position wherein the proximal end 260 of the support wire 258 is closer to the distal end 270 of the sleeve 266, as illustrated in FIG. 4. In other words, the proximal end 260 of the support wire 258 transitions to a position wherein it is distally, or more distally, spaced from the proximal end 268 of the sleeve 266. In yet other embodiments, the proximal end 260 of the support wire 258 may distally move beyond the distal end 270 of the sleeve 266 such that the support wire is no longer disposed within the sleeve. The ability of the proximal end 260 of the support wire 258 to move distally during removal of the balloon catheter assembly alleviates and/or negates many complications that are encountered in the removal process.

In some embodiments, the proximal end 212 of the elongated member 210 may be fixedly coupled to the hub 254, and the distal end 214 of the elongated member 210 may be fixedly coupled to the proximal end 222 of the inflation balloon 220. Additionally, the proximal end 260 of the support wire 258 may not be fixedly coupled with the hub 254 (i.e., the proximal end 260 of the support wire 258 may be longitudinally displaceable within at least a portion of the hub 254 or sleeve 266); however, the coupling portion 264 of the support wire 258 may be fixedly coupled to the distal end 214 of the elongated member 210 and/or the proximal end 222 of the inflation balloon 220. In such a configuration, application of a proximal longitudinal force to the hub 254 may be transferred to at least the proximal end 222 of the inflation balloon 220 via the elongated member 210, but the proximal longitudinal force may not be transferred to the inflation balloon 220 via the support wire 258. Transfer of the proximal longitudinal force to the proximal end 222 of the inflation balloon 220 via the elongated member 210 may inhibit or resist longitudinal compression of the inflation balloon 220 upon proximal displacement of the inflation balloon 220 into or through a delivery lumen and/or body lumen.

In other embodiments, the proximal end 260 of the support wire 258 may be fixedly coupled to the hub 254, and the coupling portion 264 of the support wire 258 may be fixedly coupled to the proximal end 222 of the inflation balloon 220. In such a configuration, application of a proximal longitudinal force to the hub 254 may be transferred via the support wire 258 to the proximal end 222 of the inflation balloon 220, such that the proximal longitudinal force may be applied to the proximal end 222 of the inflation balloon 220 via the support wire 258. Transfer of the proximal longitudinal force to the proximal end 222 of the inflation balloon 220 via the support wire 258 may also inhibit or resist longitudinal compression of the inflation balloon 220 upon proximal displacement of the inflation balloon 220 into or through a delivery lumen and/or body lumen. Configurations wherein the proximal longitudinal force is transferred from the hub 254 to the proximal end 222 of the inflation balloon 220 via both of the elongated member 210 and the support wire 258 are also within the scope of the present disclosure.

An illustrative method of positioning the balloon catheter assembly may comprise applying a force (i.e., by a practitioner during a medical procedure) to displace the balloon catheter assembly within a delivery lumen and/or a body lumen. The applied force can be transferred to or from the support wire such that the support wire does not exert a longitudinally compressive force on the inflation balloon. For example, as discussed above, in embodiments wherein the support wire is coupled to each of the distal end and the proximal end of the inflation balloon, the support wire can add increased rigidity and/or stiffness to the inflation balloon such that longitudinal compression of the inflation balloon may be inhibited or resisted. The method of positioning the balloon catheter assembly may further comprise deploying or inflating the inflation balloon at or adjacent to a target site. In some embodiments, the method may also comprise applying a proximal longitudinal force to the inflation balloon via the elongated member to retrieve the inflation balloon from the delivery lumen and/or the body lumen, wherein the proximal longitudinal force is not transferred to the inflation balloon via the support wire. Stated another way, the distal end of the support wire may be fixedly coupled to the inflation balloon, but the proximal end of the support wire may be longitudinally displaceable within the hub, as illustrated in FIGS. 4 and 5, such that a proximal longitudinal force may be applied to the inflation balloon via the elongated member but not via the support wire. In other embodiments, the method may comprise applying the proximal longitudinal force to a proximal end of the inflation balloon via the support wire. For example, the proximal end of the support wire may be fixedly coupled to the hub, and the coupling portion of the support wire may be fixedly coupled to the proximal end of the inflation balloon such that the proximal longitudinal force may be applied to the proximal end of the inflation balloon via the support wire.

Figure 6:
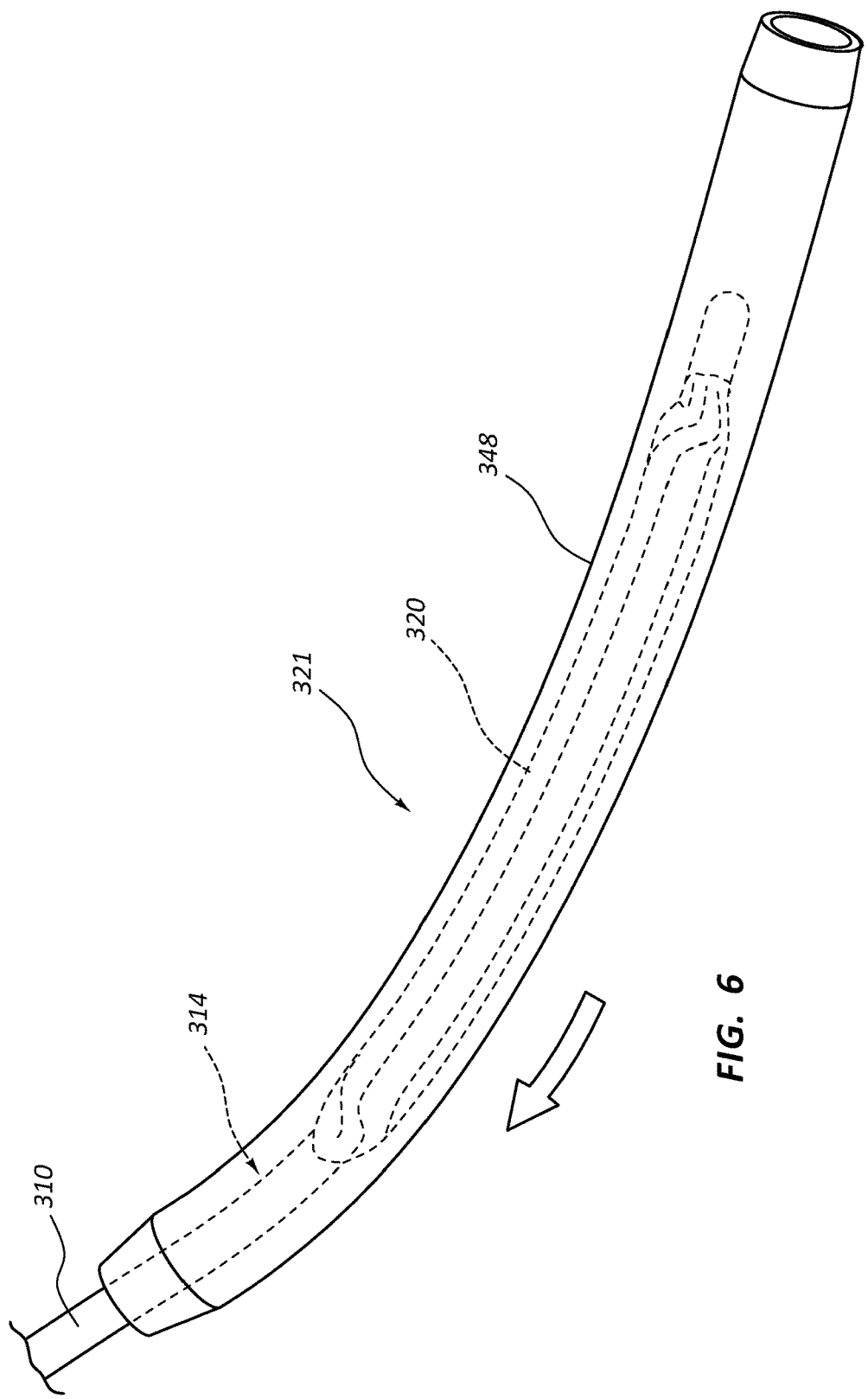
FIG. 6 is a perspective view of a portion of a balloon catheter assembly, depicted in a packaged configuration, according to yet another embodiment of the present disclosure.

FIGS. 6-9 illustrate a portion of a balloon catheter assembly, according to another embodiment of the present disclosure. As shown in FIG. 6, in some embodiments, the balloon catheter assembly comprises a sheath or covering 348 that is configured to cover the balloon segment 321 when the inflation balloon 320 is in a packaged configuration. The sheath 348 may comprise various materials, including polymeric materials. In some embodiments, the proximal and/or distal end of the sheath 348 may be flared outwardly as desired.

In the packaged configuration, the inflation balloon 320 is in a folded and deflated state. The sheath 348 is configured to be longitudinally and/or axially displaceable along the balloon segment 321 and the elongated member 310. As indicated by the reference arrow, a practitioner may remove the sheath 348 from the balloon segment 321 by sliding or otherwise moving the sheath 348 in the proximal direction along the elongated member 310. With the sheath 348 disposed at a position that is proximal to the balloon segment 321, the balloon segment 321 may be introduced into a body lumen and inflated. If desired, the practitioner can also remove the sheath 348 distally and off of the elongated member 310 entirely.

Figure 7:
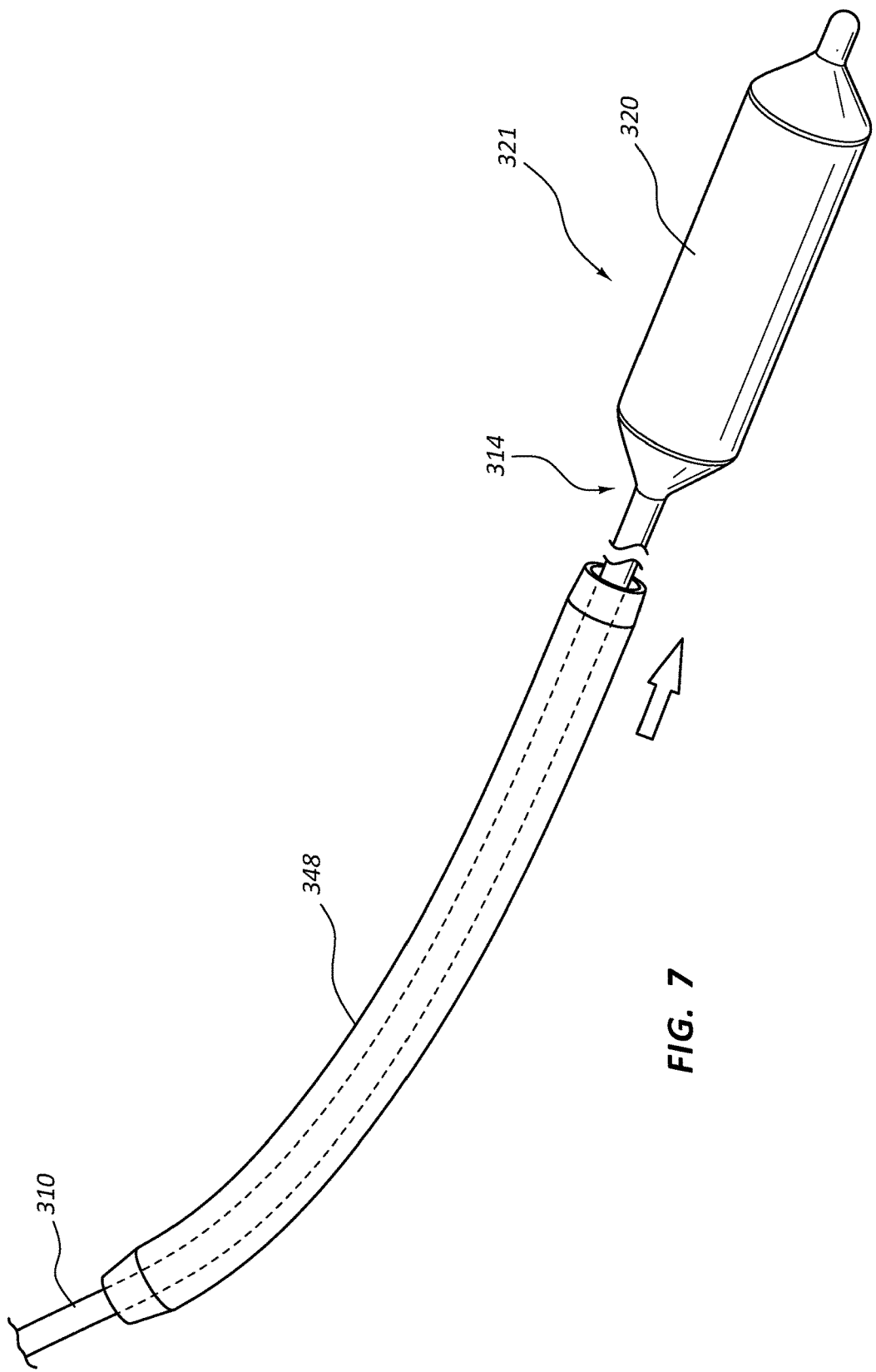
FIG. 7 is a perspective view of the portion of the balloon catheter assembly of FIG. 6, depicted in an unpackaged and inflated configuration.

FIGS. 7 and 8 illustrate the portion of the balloon catheter assembly of FIG. 6 in an unpackaged configuration, after the sheath 348 has been proximally removed from the balloon segment 321. For example, the sheath 348 is disposed around the elongated member 310 at a location that is proximal to the balloon segment 321. In FIG. 7, the inflation balloon 320 is depicted in an inflated state. After the medical procedure is completed, the practitioner may deflate the inflation balloon 320, as depicted in FIG. 8. After the medical procedure is completed, the practitioner may also remove the balloon segment 321 from the body lumen. The sheath 348 can then be moved distally (e.g., slid) to a position that covers, or partially covers, the balloon segment 321 comprising the inflation balloon 320, as indicated by the reference arrows.

FIG. 9 depicts the portion of the balloon catheter assembly of FIG. 6 in a repackaged configuration. In the repackaged configuration, the sheath 348 has been returned to a position wherein the sheath 348 is disposed around at least a portion of the balloon segment 321 and the inflation balloon 320. For example, in the illustrated embodiment, the deflated inflation balloon 320 is compressed, crumpled, forced, or otherwise folded within the sheath 348. If desired, the practitioner may remove the sheath 348 by proximally moving the sheath 348 along the elongated member 310 prior to a second medical procedure, as indicated by the reference arrow.

With continued reference to FIGS. 6-9, an illustrative method of employing the disclosed balloon catheter assembly may comprise a step of obtaining a packaged balloon catheter assembly, the packaged balloon catheter assembly comprising: an elongated member 310 having a distal end 314 that is coupled to a balloon segment 321, comprising an inflation balloon 320; and a sheath 348 disposed around the balloon segment 321, the sheath 348 being longitudinally displaceable along the balloon segment 321 and the elongated member 310. The method may further comprise a step of unpackaging the balloon catheter assembly, wherein unpackaging the balloon catheter assembly comprises longitudinally sliding the sheath 348 in a proximal direction to a position on the elongated member 310 that is proximal to the balloon segment 321. The method may further comprise a step of repackaging the balloon catheter assembly, wherein repackaging the balloon catheter assembly comprises longitudinally sliding the sheath 348 in a distal direction to a position wherein the sheath 348 is disposed around at least a portion of the balloon segment 321.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. The scope of the invention is therefore defined by the following claims and their equivalents.

What is claimed is:

1. A balloon catheter assembly, comprising:
an elongated member having a lumen extending longitudinally therethrough;
a hub coupled to a proximal end of the elongated member;
a support wire disposed within the elongated member, wherein a proximal end of the support wire is operatively coupled to the hub, such that the support wire has distal longitudinal displacement with respect to a portion of the hub; and
an inflation balloon, wherein a distal end of the inflation balloon is fixedly coupled to a distal end of the support wire, wherein the support wire is operatively coupled to the balloon catheter assembly such that the support wire does not exert a longitudinally compressive force on the inflation balloon;
a sleeve fixedly coupled to an inside of the hub, wherein the proximal end of the support wire is disposed within the sleeve, wherein the proximal end of the support wire is longitudinally displaceable within the sleeve, wherein the proximal end of the support wire is configured to be distally displaceable beyond a distal end of a sleeve, and wherein the support wire is configured to transfer distally oriented forces exerted on the hub, and
wherein the support wire is configured to not transfer a proximally oriented force exerted on the hub to the inflation balloon.

2. The balloon catheter assembly of claim 1, wherein a proximal end of the inflation balloon is coupled to a coupling portion of the support wire.

3. The balloon catheter assembly of claim 1, wherein a coupling portion of the support wire is at least partially disposed within and fixedly coupled to a tubular member and wherein the tubular member is fixedly coupled to a proximal end of the inflation balloon.

4. The balloon catheter assembly of claim 3, wherein the support wire is disposed within the lumen of the elongated member.

5. The balloon catheter assembly of claim 3, wherein at least a portion of at least one of the tubular member and the support wire comprises a radiopaque marker.

6. The balloon catheter assembly of claim 1, wherein a portion of the sleeve is offset from a central axis of the hub.

7. The balloon catheter assembly of claim 1, wherein the sleeve is at least partially disposed within the lumen of the elongated member.

8. A balloon catheter assembly, comprising:
an elongated member having a lumen extending longitudinally therethrough;
a hub coupled to a proximal end of the elongated member;
a support wire disposed within the elongated member, wherein a proximal end of the support wire is operatively coupled to the hub, such that the support wire has distal longitudinal displacement with respect to a portion of the hub; and
an inflation balloon, wherein a distal end of the inflation balloon is fixedly coupled to a distal end of the support wire, wherein the support wire is operatively coupled to the balloon catheter assembly such that the support wire does not exert a longitudinally compressive force on the inflation balloon;
wherein the support wire is configured to not transfer a proximally oriented force exerted on the hub to the inflation balloon; and
wherein a coupling portion of the support wire is at least partially disposed within and fixedly coupled to a tubular member and wherein the tubular member is fixedly coupled to a proximal end of the inflation balloon.

9. The balloon catheter assembly of claim 8, wherein the support wire is disposed within the lumen of the elongated member.

10. The balloon catheter assembly of claim 8, wherein at least a portion of at least one of the tubular member and the support wire comprises a radiopaque marker.

11. A balloon catheter assembly, comprising:
an elongated member having a lumen extending longitudinally therethrough;
a hub coupled to a proximal end of the elongated member;
a support wire disposed within the elongated member, wherein a proximal end of the support wire is operatively coupled to the hub, such that the support wire has distal longitudinal displacement with respect to a portion of the hub; and
an inflation balloon, wherein a distal end of the inflation balloon is fixedly coupled to a distal end of the support wire, wherein the support wire is operatively coupled to the balloon catheter assembly such that the support wire does not exert a longitudinally compressive force on the inflation balloon;
a sleeve fixedly coupled to an inside of the hub, wherein the proximal end of the support wire is disposed within the sleeve, wherein the proximal end of the support wire is longitudinally displaceable within the sleeve, and wherein a portion of the sleeve is offset from a central axis of the hub; and
wherein the support wire is configured to not transfer a proximally oriented force exerted on the hub to the inflation balloon.

* * * * *